(12) United States Patent
Brugger

(10) Patent No.: US 8,210,049 B2
(45) Date of Patent: Jul. 3, 2012

(54) PRESSURE MEASUREMENT DEVICE

(75) Inventor: James M. Brugger, Newburyport, MA (US)

(73) Assignee: NXSTAGE Medical, Inc., Lawrence, MA (US)

(*) Notice: Subject to any disclaimer, the term of this patent is extended or adjusted under 35 U.S.C. 154(b) by 1143 days.

(21) Appl. No.: 12/049,903

(22) Filed: Mar. 17, 2008

(65) Prior Publication Data

US 2008/0228087 A1 Sep. 18, 2008

Related U.S. Application Data

(60) Provisional application No. 60/894,926, filed on Mar. 15, 2007.

(51) Int. Cl.
*G01L 7/08* (2006.01)
*A61B 5/021* (2006.01)

(52) U.S. Cl. .......................................... 73/715; 600/485

(58) Field of Classification Search ............. 73/700–756
See application file for complete search history.

(56) References Cited

U.S. PATENT DOCUMENTS

| | | | |
|---|---|---|---|
| 3,713,341 A | 1/1973 | Madsen et al. |
| 3,981,197 A | 9/1976 | Lieber et al. |
| 4,314,480 A | 2/1982 | Becker |
| 4,398,542 A | 8/1983 | Cunningham et al. |
| 5,195,522 A | 3/1993 | Pytel et al. |
| 5,284,150 A | 2/1994 | Butterfield et al. |
| 5,450,852 A | 9/1995 | Archibald |
| 5,693,008 A | 12/1997 | Brugger et al. |
| 6,117,086 A | 9/2000 | Shulze |
| 2006/0278001 A1 | 12/2006 | Kaneko et al. |
| 2007/0179422 A1 | 8/2007 | Schnell et al. |

*Primary Examiner* — Andre Allen
(74) *Attorney, Agent, or Firm* — Miles & Stockbridge, P.C.; Mark A. Catan

(57) ABSTRACT

A pressure measurement device isolates liquid, such as blood, from an intermediate fluid, such as air, by means of a diaphragm. The diaphragm is arranged between first and second chambers of respective first and second shells of a pressure pod body. The first shell has first and second ports, which are connected to the first chamber. The second shell has a measurement port with a connector in communication with the second chamber. A pressure transducer with a mating connector is directly connected to the measurement port connector to minimize the sealed volume between the diaphragm and the pressure transducer.

23 Claims, 2 Drawing Sheets

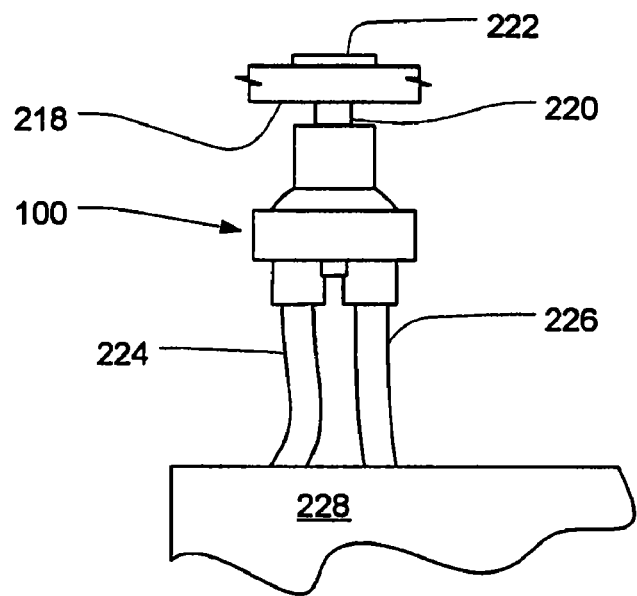
Fig. 3
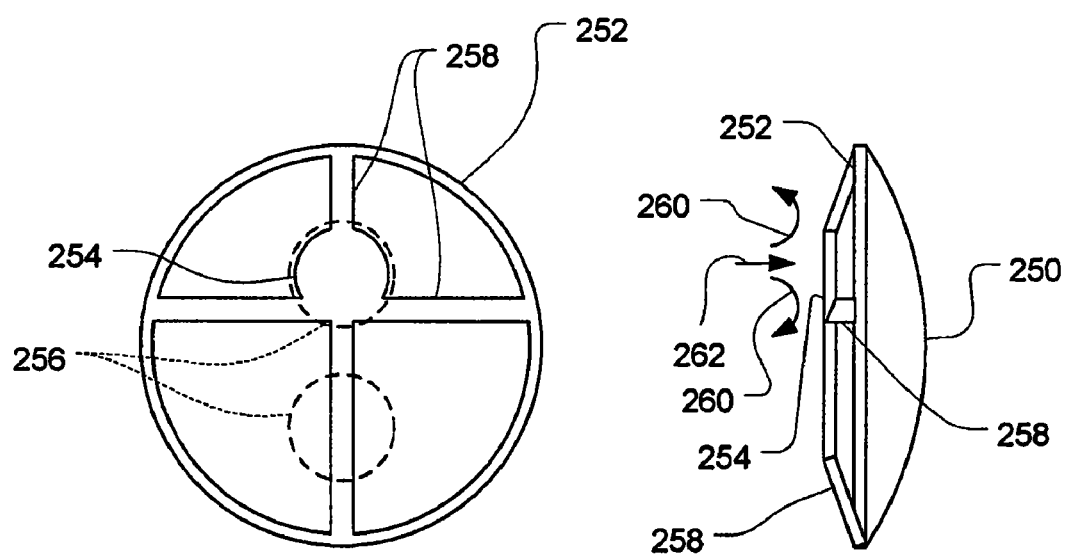
Fig. 4A                    Fig. 4B

PRESSURE MEASUREMENT DEVICE

CROSS-REFERENCE TO RELATED APPLICATIONS

The present application claims the benefit under 35 U.S.C. §119(e) of U.S. Provisional Patent Application No. 60/894,926, filed Mar. 15, 2007, entitled "Pressure Measurement Device", which is incorporated herein by reference in its entirety.

FIELD OF THE INVENTION

The present invention relates to pressure measurement devices and more particularly to devices that permit pressure measurement while isolating the pressure transducer and/or medium in contact therewith, from the fluid whose pressure is to be measured.

BACKGROUND

FIG. 1 shows a pressure measurement pod 10. In the pod 10, air chamber 45 is in communication with an air port 12 and air line 40 that can be connected to a pressure transducer (not shown). Fluid flows through a fluid chamber 60 between an inlet line 35 connected to an inlet port 70 and out of the fluid chamber 60 through an outlet port 72 into an outlet line 15. The pressure of the fluid in the fluid chamber 60 displaces a diaphragm 25 until the air chamber 45 and fluid chamber 60 are at equilibrium, which is preferably the situation when the air and fluid chambers 45 and 60 are at equal pressure.

The pod 10 is primarily made of two parts, a fluid-side shell 30 and an air-side shell 17, that, together, form an enclosure 5 that defines the fluid and air chambers 60 and 45. The ratio of the minimum to the maximum volume of the air chamber 45, including the volume of the line 40 and port 12, is proportional to the total pressure variation that can be measured by the transducer attached to the line 40. The fixed volume defined by the line 40 and port 12 serves as a limit on this ratio and therefore limits the pressure range that can be measured. Another feature of the pod 10 is that the fluid shell must be formed by a mold that has more than two parts, because of the inlet and outlet ports 70 and 72 and the recess that helps define the fluid chamber 60. Since molds with more than two parts are more expensive to design and make, this is a disadvantage.

Another feature of the pod 10 is the orientation of the inlet and outlet lines 35 and 15 owing to those of the inlet and outlet ports 70 and 72. The orientations require the pod 10 be placed in a straight run of tubing, which can make it difficult to design a compact fluid circuit assembly in which the pod is used. Yet another feature is the use of an intermediate line 40 between the transducer and the pod 10, which makes the pod assembly larger, requires more parts to be assembled, and has more seals which may fail. Another feature of prior art pods in general is the use of diaphragms that are more permeable than may be desirable. Also, the attachment between the blood side shell 30 and the air side shell 17 may be made by a compression seal (details not shown) or by another means of attachment, but in any event, may require additional steps to seal the diaphragm within.

SUMMARY

Embodiments of the present invention may address the above-mentioned disadvantages and limitations, among other things. The present invention includes a pod, which may be employed for pressure measurement in a blood treatment tubing set, such as described in U.S. Pat. No. 5,693,008, which is hereby incorporated by reference as if fully set forth in its entirety herein. In such a blood treatment tubing set, the pod may be configured to support high flow rates of fluid, as may be necessary for a blood treatment process, such as dialysis. The pod may be formed from two shells which may be sealed together with a diaphragm between them. The diaphragm may be sandwiched between the two shells so as to form a seal. The diaphragm may be pinched between the two shells along its periphery. Each shell of the pod defines a respective chamber in concert with a respective side of the diaphragm. One of the shells preferably has a pair of ports to allow fluid into and out of one of the chambers, which is the fluid chamber. It is advantageous for the latter shell's two ports to be arranged such that the shell can be formed using a two-part mold, at least because of the tooling costs savings. In that case, the two ports may be configured such that they have parallel axes. The two ports may also be on the same side of the fluid chamber. The two ports may also be at right angles with respect to the diaphragm. In the latter arrangement, fluid is forced to make a U-turn which in turn promotes turbulence and minimizes stagnant regions of the fluid chamber.

Another feature is that a large range of pressures may be measured by particular embodiments, in which provision is made for defining a minimal volume between the pressure transducer and an air side of the diaphragm, when the one of the chambers opposite the fluid chamber (i.e., the air chamber) is expanded to its maximum size by displacement, and concomitant deformation, of the diaphragm. The minimal volume may be achieved by locating the pressure transducer connector and the pressure transducer adjacent the air chamber. Thus, a high ratio of the size of the expanded air chamber to the collapsed air chamber can be achieved.

Another feature is the use of a diaphragm of polyvinyl chloride (PVC), which has very low air permeability. The PVC diaphragm may be in the form of a sheet having a thickness, over a major portion thereof, of between 5 and 20 mil, inclusive. For example, the diaphragm may have a thickness of 10 mil (1/100 inch). In an exemplary embodiment, the diaphragm is held in place by adhesively bonding the two shells together. In such a configuration, the shells may be constructed to provide a large surface area for bonding, which preferably forms somewhat of a slide-fit to give high rigidity to the bonded parts.

In certain embodiments, an access port may be provided on the fluid-side of the diaphragm and opening to the fluid chamber. In applications where blood is the fluid being measured, the access port may allow for blood to be sampled or for medication or medicaments to be injected into the blood flow without the need to provide an additional component.

According to an embodiment of a pressure measurement device, a pod body may have a first shell, a second shell, a diaphragm, and a deflector unit. The diaphragm may be pinched at its periphery between the first shell and the second shell so as to form a first chamber in the first shell and a second chamber in the second shell. The first and second chambers may be separated by the diaphragm. The first shell may have a first port and a second port in fluid communication with the first chamber. The second shell may have a measurement port in fluid communication with the second chamber. The measurement port may include a connector adjacent the second chamber. The deflector unit may be arranged to redirect fluid flowing into the first chamber so as to prevent fluid momentum from displacing the diaphragm.

At least the first shell may be shaped such that it can be molded in and removed from a rigid two-part mold. In other words, the shape of the first shell may be such that it is possible for the rigid two-part mold to be removed from the first shell without breaking the two-part mold or the first shell even if a material of the first shell is rigid after molding. The pod second shell may also be shaped such that it can be molded in a two-part mold. In other words, the second shell may also be shaped such that a two-part mold can be removed from the molded second shell without breaking the two-part mold or the molded second shell, even if the material used for the second shell is rigid after molding.

The second shell may have an apron that forms a recess into which the first shell fits. The first shell may have a third port that is in communication with the first chamber. The third port may be smaller than either of the first or second ports. The first and second shells may be solvent bonded together. The first and second shells may be of flexible polymer material to, for example, promote sealing when bonded together. The device may be incorporated in a blood tubing set such that the first and second ports are connected to respective blood lines of the blood tubing set.

The first and second ports may have respective axes that are parallel. In such a case, the ports may be located on the same side of the first shell with respect to the first chamber. The first and second ports may be shaped such that fluid flowing from the first port and into the second port must substantially reverse direction in going from the first port to the second port. In this way, turbulence may be promoted. The configuration also lends itself to two-part molding. The diaphragm may form a flat sheet and the first and second ports may have respective axes that are mutually parallel and perpendicular to the diaphragm. The second shell may have a second chamber surface, which faces the diaphragm, with a concave shape such that the diaphragm can conform to second chamber surface.

A pressure transducer may be connected to the measurement port connector with no intervening parts. The pressure transducer may be provided with a mating connector that directly connects the pressure transducer to the connector of the measurement port. The measurement port connector may include a luer connector adjacent the second chamber. The measurement port may include a luer connector which forms a shell or a part of the second shell, although other types of connectors may be used for the measurement port connector. For example, the measurement port may include a male luer which forms a shell or a part of the second shell. For example, the pressure transducer may have affixed thereto a female luer that connects directly to the male luer with no intervening components. The pressure transducer may have affixed thereto a female luer that connects directly to the male luer with no intervening components and such that the pressure transducer is rigidly connected to the male luer.

The pressure transducer may be connected to seal the measurement port such that a sealed volume is defined by the second chamber and pressure transducer. The sealed volume can be changed between a maximum value and a minimum value by displacing the diaphragm. In that case, the ratio of the maximum to minimum volume is, preferably, at least 5 and, more preferably, at least 10 and, even more preferably, at least 15. Displacement of the diaphragm to change the sealed volume may occur prior to connecting the pressure transducer.

The diaphragm may be made of polyvinyl chloride. The second chamber may have a dome-shaped side with an apex. The measurement port may be located at the apex. A pressure transducer may be rigidly affixed to the measurement port. The diaphragm of polyvinyl chloride may have a thickness, over at least a major portion thereof, of between 5 mil and 20 mil, inclusive. For example, the thickness of the PVC diaphragm may be 10 mil. The first and second ports may be shaped to define cylindrical recesses to permit tubing to be adhesively bonded therewithin. In that case, each of the first and second port recesses may have an axis which is substantially parallel. The first and second port recesses may be located on the same side of the first shell. The second shell may include an integral male luer.

The deflector unit may have a deflector plate positioned in a flow path from the inlet port. The deflector plate may be configured to dissipate fluid flowing from the inlet port into eddies instead of directly impacting the diaphragm. The deflector plate may be held in place in the first chamber by one or more supports extending from a periphery of the deflector unit. The deflector unit may have sufficient open space between supports to avoid dead zones for fluid stagnation. For example, the open space between supports may be greater than 50%. The deflector plate and the supports may be dished, or biased, towards the first shell. In other words, the deflector plate and the supports may be arranged farther from the diaphragm than a periphery of the deflector unit.

According to another embodiment of a pressure measurement device, a pod body may have a first shell, a second shell, and a diaphragm between the first and second shells so as to form first and second chambers separated by the diaphragm. The first shell may have a first port and a second port in communication with the first chamber. The second shell may have a measurement port with an integral connector that is in communication with the second chamber. The second shell may be constructed such that a pressure transducer may be directly connected to the measurement port to define a sealed volume between the pressure transducer and the diaphragm. The sealed volume may transfer pressure from the diaphragm to the pressure transducer.

At least the first shell may be shaped such that it can be molded in and removed from a rigid two-part mold. In other words, the shape of the first shell may be such that it is possible for the rigid two-part mold to be removed from the first shell without breaking the two-part mold or the first shell even if a material of the first shell is rigid after molding. The pod second shell may also be shaped such that it can be molded in a two-part mold. In other words, the second shell may also be shaped such that a two-part mold can be removed from the molded second shell without breaking the two-part mold or the molded second shell, even if the material used for the second shell is rigid after molding.

The second shell may have an apron that forms a recess into which the first shell fits. The first shell may have a third port that is in communication with the first chamber. The third port may be smaller than either of the first or second ports. The first and second shells may be solvent bonded together. The first and second shells may be of flexible polymer material to, for example, promote sealing when bonded together. The device may be incorporated in a blood tubing set such that the first and second ports are connected to respective blood lines of the blood tubing set.

The first and second ports may have respective axes that are parallel. In such a case, the ports may be located on the same side of the first shell with respect to the first chamber. The first and second ports may be shaped such that fluid flowing from the first port and into the second port must substantially reverse direction in going from the first port to the second port. In this way, turbulence may be promoted. The configuration also lends itself to two-part molding. The diaphragm may form a flat sheet and the first and second ports may have respective axes that are mutually parallel and perpendicular to the diaphragm. The second shell may have a second chamber surface, which faces the diaphragm, with a concave shape such that the diaphragm can conform to second chamber surface.

A pressure transducer may be connected to the measurement port connector with no intervening parts. The pressure transducer may be provided with a mating connector that directly connects the pressure transducer to the connector of the measurement port. The measurement port connector may include a luer connector adjacent the second chamber. For example, the measurement port may include a luer connector which forms a shell or a part of the second shell. For example, the measurement port may include a male luer which forms a shell or a part of the second shell. For example, the pressure transducer may have affixed thereto a female luer that connects directly to the male luer with no intervening components. For example, the pressure transducer may have affixed thereto a female luer that connects directly to the male luer with no intervening components and such that the pressure transducer is rigidly connected to the male luer.

The pressure transducer may be connected to seal the measurement port such that a sealed volume is defined by the second chamber and pressure transducer. The sealed volume can be changed between a maximum value and a minimum value by displacing the diaphragm. In that case, the ratio of the maximum to minimum volume is, preferably, at least 5 and, more preferably, at least 10 and, even more preferably, at least 15. Displacement of the diaphragm to change the sealed volume may occur prior to connecting the pressure transducer. The sealed volume may be filled with a fluid, for example, air.

The diaphragm may be pinched at its periphery between the first shell and the second shell so as to form a first chamber in the first shell and a second chamber in the second shell. The diaphragm may be made of polyvinyl chloride. The second chamber may have a dome-shaped side with an apex. The measurement port may be located at the apex. A pressure transducer may be rigidly affixed to the measurement port. The diaphragm of polyvinyl chloride may have a thickness, over at least a major portion thereof, of between 5 mil and 20 mil, inclusive. For example, the thickness of the PVC diaphragm may be 10 mil. The first and second ports may be shaped to define cylindrical recesses to permit tubing to be adhesively bonded therewithin. In that case, each of the first and second port recesses may have an axis which is substantially parallel. The first and second port recesses may be located on the same side of the first shell. The second shell may include an integral male luer.

A deflector unit may also be provided to redirect fluid flowing into the first chamber so as to prevent fluid momentum from displacing the diaphragm. The deflector unit may have a deflector plate positioned in a flow path from the inlet port. The deflector plate may be configured to dissipate fluid flowing from the inlet port into eddies instead of directly impacting the diaphragm. The deflector plate may be held in place in the first chamber by one or more supports extending from a periphery of the deflector unit. The deflector unit may have sufficient open space between supports to avoid dead zones for fluid stagnation. For example, the open space between supports may be greater than 50%. The deflector plate and the supports may be dished, or biased, towards the first shell. In other words, the deflector plate and the supports may be arranged farther from the diaphragm than a periphery of the deflector unit.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention. Throughout the figures, like reference numerals denote like elements.

FIG. 3 shows the pressure measurement pod of FIG. 2 attached to a fluid circuit.

FIG. 4A shows a face view of a fluid momentum deflector which may optionally be used with the pressure measurement pod of FIG. 2.

FIG. 4B shows an edge view of the fluid momentum deflector of FIG. 4A.

DETAILED DESCRIPTION

Figure 2:
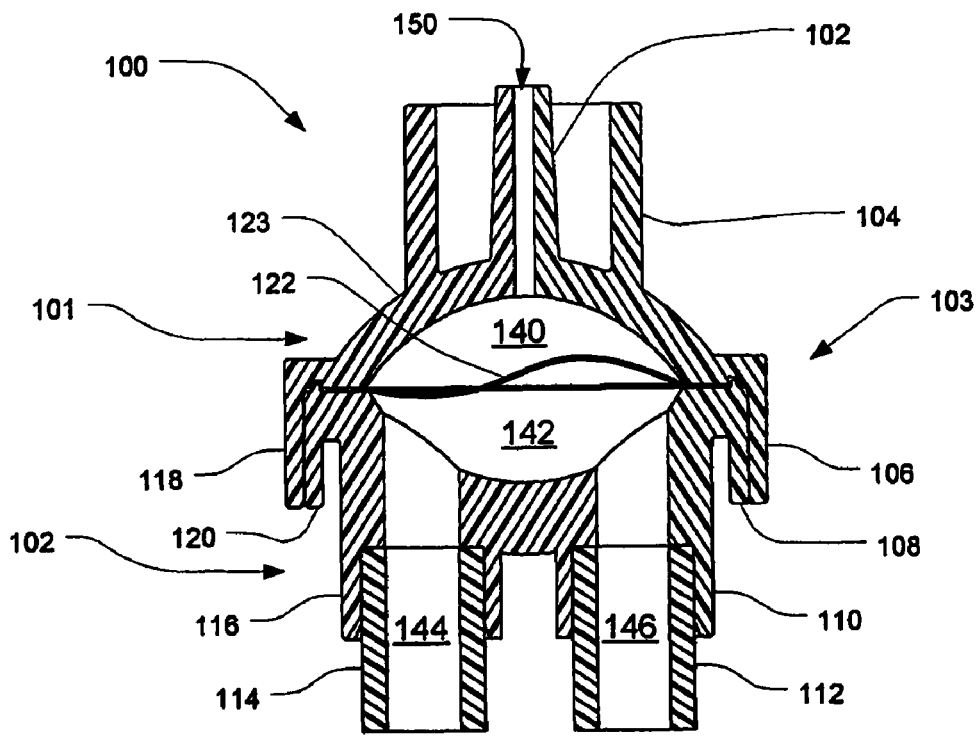
FIG. 2 shows a pressure measurement pod according to an exemplary embodiment of the present invention.

FIG. 2 shows a pressure measurement pod 100 according to an exemplary embodiment of the present invention. An air chamber 140 is in communication with a measurement port 150 which is part of an integral connector 102 that can be directly connected to a pressure transducer (not shown) with a mating connector. In an exemplary embodiment, connector 102 is a male luer connector and the mating connector is a female luer connector. However, the connectors are not limited to these descriptions. Any other known mating connectors suitable for making sealed fluid connections may be used for the connectors in the various embodiments.

Fluid flows through a fluid chamber 142 between an inlet line 114 connected to an inlet port 144 and out of the fluid chamber 142 through an outlet port 146 into an outlet line 112. The fluid chamber 142 may be configured to have a flow path cross-section similar to that of the inlet port and the outlet port. In particular, the fluid chamber may be configured to minimize obstructions in the flow from the inlet port to the outlet port so as to be able to support higher flow rates, such as may be seen with certain blood treatment systems.

The pressure of the fluid in the fluid chamber 142 displaces a diaphragm 122 until the air chamber 140 and fluid chamber 142 are at equilibrium, which is preferably the situation when the air and fluid chambers 140 and 142 are at equal pressure. Thus, the air chamber 140, together with the volume in the measurement port 150 between the pressure transducer and the air chamber 140, defines a sealed volume which acts to transmit the displacement of the diaphragm caused by the pressure in the fluid chamber 142 to the pressure transducer. This sealed volume may be filled with a fluid, preferably air. However, any other fluid medium may also be used to fill the sealed volume, as appropriate.

It should be evident that although ports 144 and 146 are referred to herein as inlet and outlet, these labels have been adopted for description purposes. The direction of fluid flow could be reversed and the labels changed accordingly without changing the function of the pressure measurement pod 100. It is also contemplated that fluid may not flow in one port and out the other port. Instead, both ports may serve as inlets for measuring the pressure of a static fluid. It is also noted that while chambers 140 and 142 are referred to herein as air chamber and fluid chamber, these labels have been adopted for description purposes. Accordingly, it is contemplated that any medium (e.g., air, fluid, etc.) may be provided in air or fluid chambers as appropriate. For example, the air chamber may be filled with a fluid and the fluid chamber may have an air-flow flowing therethrough.

Figure 1:
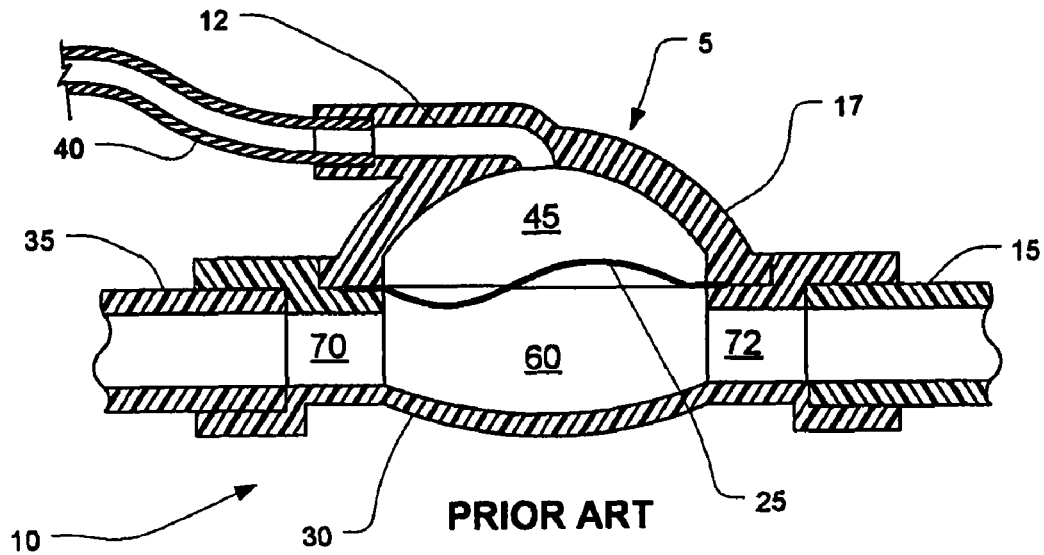
FIG. 1 shows a pressure measurement pod according to the prior art.

The pod 100 is primarily made of two parts, a fluid-side shell 102 and an air-side shell 101, that, together, form an enclosure 103 that defines the fluid and air chambers 142 and 140, respectively. The ratio of the minimum to the maximum volume of the air chamber 140, including the volume of the measurement port 150, is proportional to the total pressure variation that can be measured by the transducer attached to the port 150. The fixed volume defined by the port 150 is kept small by virtue of the connection of the pressure transducer proximal to the air chamber 140 and therefore is not a severe limit on this ratio. In other words, a pressure transducer may be rigidly connected to the measurement port 150 with no intervening connections so as to minimize the volume of air in measurement port 150. For example, the pressure transducer may be located such that the length of the path between the pressure transducer and the air chamber is less than 5 cm. Thus, the fixed volume of the air chamber and measurement port does not limit the pressure range that can be measured as much as the configuration shown in FIG. 1.

Another feature of the pod 100 is that the fluid shell 102 can be formed by a mold that has only two parts, because of the configuration of the inlet and outlet ports 144 and 146 and the recess that helps define the fluid chamber 142. Since molds with more than two parts are more expensive to design and make, this is an advantage.

Another feature of the pod 100 is the orientation of the inlet and outlet lines 114 and 112 owing to those of the inlet and outlet ports 144 and 146. The orientations permit the pod 100 to be placed in transverse extensions of tubing, which can make it easier to design a compact fluid circuit assembly in which the pod is used.

Yet another feature of the pod 100 is the lack of an intermediate line between the transducer and the pod 100, which makes the pod assembly smaller and reduces the number of parts to be assembled as well as reducing the number of seals which may fail.

Yet another feature of pod 100 is that the diaphragm 122 may be made from PVC, which is less permeable than prior art materials. In an exemplary embodiment, the diaphragm may be pressure sealed by adhering a skirt 118 of one of the shells to the other.

In certain embodiments, the components of the pressure measurement pod 100 may be configured for one-time use, i.e. disposable. The pressure transducer attached to the pod 100 may also be disposable. Alternately, the pressure measurement pod 100 may be used in conjunction with a permanent or reusable pressure transducer. The disposable nature of the pressure measurement pod 100 is especially useful for medical device applications which require a sterile fluid path.

FIG. 3 shows an embodiment of pressure measurement pod, such as that shown in FIG. 2, attached to a fluid circuit 228. The parallel inlet 224 and outlet 226 lines are adjacent each other and connect to a fluid circuit 228. The pressure measurement pod 100 is shown connected to a permanent transducer 222, which may be attached to the frame 218 of a permanent fixture. In a preferred application, the pressure measurement pod may be used with a medical treatment or blood treatment device. In many of these devices, the fluid circuit 228 is a disposable unit and would need to be attached to a permanent pressure transducer 222 each time the fluid circuit 228 is replaced for a new treatment. As previously discussed, fluid flowing through pod 100 may be blood in a blood treatment application and, thus, require high sterility for the fluid circuits. The configuration of the lines 224 and 226 allows the transducer to be handled and attached easily. Particularly in embodiments where the pressure measurement pod 100 is small, the operator's hand can easily wrap around the pressure measurement pod 100 and lines 224 and 226.

FIG. 4A shows a face view of a fluid momentum deflector which may optionally be used with the pressure measurement pod of FIG. 2. FIG. 4B shows an edge view of the fluid momentum deflector of FIG. 4A. Because fluid flowing into and out of the fluid chamber 142 (FIG. 2) must reverse direction, a significant change in momentum may occur at high flow rates. If the fluid is deflected directly by the diaphragm 122, error may be introduced into the pressure measurement, depending on the requirements of the particular application. To address these concerns, a deflector unit 252 may hold a deflector plate 254 in position over the inlet 256 (corresponding to the inlet 144 of FIG. 2) such that a jet 262 of fluid emanating from the inlet 256 is deflected by the deflector plate. Thus, jet 262 dissipates into eddies 260 rather than impacting and displacing the diaphragm 250. While the deflector plate 254 may serve to redirect the momentum of the flow, it may also be configured so as to not significantly obstruct the flow such that the pod may still be used at higher flow rates in certain applications (e.g., blood tubing sets in dialysis procedures). Supports 258 may hold the deflector plate 254 while creating a large open area for fluid movement thereby avoiding dead zones where fluid may stagnate. The supports may extend from a periphery of the deflector unit 252 into the fluid chamber. Preferably the open area between the supports 258 is greater than 50%. The deflector unit 252 may be made such that it seals along with the diaphragm as a layered set of elements that can be compression sealed together with the air and fluid shells 123 and 120. Alternatively the deflector unit can be made smaller such that it fits inside the fluid shell 120 without sealing to the edges of the shells. The deflector unit may be integrated with the diaphragm. The supports 258 may be made such that supports 258 and deflector plate 254 are dished toward the liquid shell so that the diaphragm 250 has a greater range of deflection. In other words, the supports 258 may extend away from the diaphragm into the fluid chamber so as to hold the deflector plate 254 at a position farther from the diaphragm than the periphery of the deflector unit.

While the present invention has been described in conjunction with a number of embodiments, the invention is not to be limited to the description of the embodiments contained herein, but rather is defined by the claims appended hereto and their equivalents. It is further evident that many alternatives, modifications, and variations would be or are apparent to those of ordinary skill in the applicable arts. Accordingly, Applicant intends to embrace all such alternatives, modifications, equivalents, and variations that are within the spirit and scope of this invention.

What is claimed is:

1. A pressure measurement device comprising:
   a pressure pod body including:
   first and second chambers separated by a flexible diaphragm;
   first and second ports in fluid communication with the first chamber, each of the first and second ports being adjacent and having a respective axis and a respective fitting for attaching to a respective tube,
   said axes being parallel such that, when each of the first and second ports is connected to the respective tube, the respective tubes are held mutually adjacent and in a parallel orientation; and
   a measurement port with an integral connector in fluid communication with the second chamber, the measurement port having a measurement port axis parallel to the first and second port axes;

the measurement port connector being configured to be engaged with a mating connector by displacing the pressure pod body in a direction aligned with the measurement port axis.

2. The pressure measurement device of claim 1, wherein the measurement port connector includes a luer connector.

3. The pressure measurement device of claim 1, wherein the measurement port connector is configured such that a pressure transducer can be directly connected thereto so as to define a sealed volume between the pressure transducer and the diaphragm, the sealed volume transferring pressure from the first chamber to the pressure transducer via the diaphragm.

4. The pressure measurement device of claim 3, wherein said sealed volume is filled with air.

5. The pressure measurement device of claim 1, further comprising a pressure transducer having the mating connector connected directly to the measurement port connector with no intervening fluid channel, the pressure transducer being attached rigidly to the measurement port connector.

6. The pressure measurement device of claim 1, wherein a surface of the second chamber facing the diaphragm has a concave shape, the diaphragm conforming to the second chamber surface at a maximum displacement of the diaphragm.

7. The pressure measurement device of claim 1, wherein the pressure pod body further includes a deflector configured to redirect dynamic pressure of fluid flowing into the first chamber thereby reducing displacement of the diaphragm by the dynamic pressure.

8. A pressure measurement device, comprising:
a first pod body shell having a first port and a second port;
a second pod body shell having a measurement port with a connector;
a diaphragm arranged between the first pod body shell and the second pod body shell so as to define a first chamber with the first pod body shell and a second chamber with the second pod body shell, the first and second chambers being separated by the diaphragm; and
a pressure transducer which is connected directly to the measurement port connector with no intervening fluid channels,
wherein the first and second ports are in fluid communication with the first chamber, and
the measurement port is in fluid communication with and adjacent to the second chamber.

9. The pressure measurement device of claim 8, further comprising a deflector unit arranged within the first chamber so as to redirect fluid which flows into the first chamber.

10. The pressure measurement device of claim 9, wherein the deflector unit includes a deflector plate supported in the first chamber so as to dissipate an inlet flow from one of the first and second ports into eddies.

11. The pressure measurement device of claim 8, wherein the pressure transducer is connected to the measurement port connector so as to define a sealed fluid volume, a volume of the sealed fluid volume is changed between a maximum value and a minimum value by displacing the diaphragm, and a ratio of the maximum value to the minimum value is at least 5.

12. The pressure measurement device of claim 8, wherein the second pod body shell has a second chamber surface facing the diaphragm, the second chamber surface having a concave shape.

13. The pressure measurement device of claim 8, wherein the diaphragm is a polyvinyl chloride sheet with a thickness, over at least a major portion thereof, of 10 mil.

14. The pressure measurement device of claim 8, further comprising a blood tubing set, the first and second ports being connected to respective blood lines of the blood tubing set.

15. A pressure measurement device, comprising:
a pressure pod body having a first shell with a first recess, a second shell with a second recess, and a diaphragm arranged between the first and second shells so as to isolate the first recess from the second recess,
the first shell having inlet and outlet ports communicating with the first recess,
the second shell having a single measurement port with a connecting portion arranged on an exterior surface of the second shell, the single measurement port communicating with the second recess; and
a measurement assembly including a pressure transducer connected releasably to said connecting portion so as to define a sealed volume between the pressure transducer and the diaphragm, the sealed volume transferring pressure from the diaphragm to the pressure transducer,
wherein said pressure pod body is removable from the measurement assembly such that the measurement assembly can be reused with a new pressure pod body.

16. The pressure measurement device of claim 15, wherein the pressure transducer is mounted on a rigid frame, the pressure pod body being supported at least in part by the connection between the pressure transducer and the connecting portion.

17. The pressure measurement device of claim 15, wherein the second recess in the second shell has a concave surface facing the diaphragm.

18. The pressure measurement device of claim 15, further comprising a blood tubing set, the inlet and outlet ports being connected to respective blood lines of the blood tubing set.

19. A pressure measurement device comprising:
a pressure pod body including:
first and second chambers separated by a flexible diaphragm;
first and second ports in fluid communication with the first chamber, each of the first and second ports being adjacent and having a respective axis and a respective fitting for attaching to a respective tube,
said axes being parallel such that, when each of the first and second ports is connected to the respective tube, the respective tubes are held mutually adjacent and in a parallel orientation; and
a measurement port with an integral connector in fluid communication with the second chamber, the measurement port having a measurement port axis parallel to the first and second port axes; and
a frame rigidly supporting a pressure transducer, the pressure transducer having a mating connector configured to connect directly to the measurement port connector such that the pressure pod is rigidly attached to the frame with no intervening fluid channel,
wherein the measurement port connector is configured to be engaged with the mating connector by displacing the pressure pod in a direction aligned with the measurement port axis, and
the mating and measurement port connectors are configured such that the first and second port respective axes extend away from the frame, whereby the pressure pod body and tubes attached to the first and second ports can be manually grasped by wrapping a single human hand therearound.

20. The pressure measurement device of claim 19, wherein the measurement port connector includes a luer connector.

21. The pressure measurement device of claim 19, wherein the pressure transducer defines a sealed volume between the pressure transducer and the diaphragm when the mating connector is connected to the measurement port connector, said sealed volume being filled with air.

22. The pressure measurement device of claim 19, wherein a surface of the second chamber facing the diaphragm has a concave shape, the diaphragm conforming to the second chamber surface at a maximum displacement of the diaphragm.

23. The pressure measurement device of claim 19, wherein the pressure pod body further includes a deflector configured to redirect dynamic pressure of fluid flowing into the first chamber thereby reducing displacement of the diaphragm by the dynamic pressure.

* * * * *